US00PP16233P2

(12) United States Plant Patent
Post

(10) Patent No.: US PP16,233 P2
(45) Date of Patent: Feb. 7, 2006

(54) ***CHRYSANTHEMUM* PLANT NAMED 'ZEMBLA SUNNY'**

(50) Latin Name: *Chysanthemum×morifolium*
Varietal Denomination: Zembla Sunny

(75) Inventor: Arie Gerard Post, 's-Gravenzande (NL)

(73) Assignee: Deliflor Royalties, B.V., Maasdijk (NL)

( * ) Notice: Subject to any disclaimer, the term of this patent is extended or adjusted under 35 U.S.C. 154(b) by 83 days.

(21) Appl. No.: 10/920,854

(22) Filed: Aug. 18, 2004

(51) Int. Cl.
*A01H 5/00* (2006.01)

(52) U.S. Cl. ..... Plt./289
(58) Field of Classification Search ..... Plt./289
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Zembla Sunny', characterized by its decorative-type inflorescences with dark yellow-colored ray florets; freely flowering habit; early and uniform flowering response; and good postproduction longevity.

1 Drawing Sheet

Botanical classification/cultivar designation: *Chrysanthemum×morifolium* cultivar Zembla Sunny.

BACKGROUND OF THE INVENTION

The present invention relates to a new and distinct cultivar of *Chrysanthemum* plant, botanically known as *Chrysanthemum×morifolium* and referred to by the name 'Zembla Sunny'.

The new *Chrysanthemum* is a naturally-occurring whole plant mutation of the *Chrysanthemum* cultivar Zembla, disclosed in U.S. Plant Pat. No. 14,052. The new *Chrysanthemum* was discovered and selected by the Inventor on Jun. 18, 2002 within a population of flowering plants of the cultivar Zembla in a controlled environment in 's Gravenzande, The Netherlands.

Asexual reproduction of the new *Chrysanthemum* by terminal cuttings in a controlled environment in 's Gravenzande, The Netherlands since Jul. 18, 2002, has shown that the unique features of this new *Chrysanthemum* are stable and reproduced true to type in successive generations.

BRIEF SUMMARY OF THE INVENTION

The cultivar Zembla Sunny has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Zembla Sunny'. These characteristics in combination distinguish 'Zembla Sunny' as a new and distinct cultivar:

1. Decorative-type inforescences with dark yellow-colored ray florets; typically grown as a spray-type.
2. Freely flowering habit.
3. Early and uniform flowering response.
4. Good postproduction longevity.

Plants of the new *Chrysanthemum* can be compared to plants of the parent, the cultivar Zembla. In side-by-side comparisons conducted in 's Gravenzande, The Netherlands, plants of the new *Chrysanthemum* differed from plants of the cultivar Zembla in the following characteristics:

1. Plants of the new *Chrysanthemum* were not as vigorous as plants of the cultivar Zembla.
2. Plants of the new *Chrysanthemum* had smaller inflorescences than plants of the cultivar Zembla.
3. Plants of the new *Chrysanthemum* and the cultivar Zembla differed in ray floret coloration as plants of the cultivar Zembla had white-colored ray florets.

Plants of the new *Chrysanthemum* can also be compared to plants of the *Chrysanthemum* cultivar Zembla Yellow, disclosed in U.S. Plant Pat. No. 14,733. In side-by-side comparisons conducted in 's Gravenzande, The Netherlands, plants of the new *Chrysanthemum* differed primarily from plants of the cultivar Zembla Yellow in the following characteristics:

1. Plants of the new *Chrysanthemum* had smaller inflorescences than plants of the cultivar Zembla Yellow.
2. Plants of the new *Chrysanthemum* and the cultivar Zembla Yellow differed in ray floret coloration as plants of the cultivar Zembla Yellow had lighter yellow-colored ray florets.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual color of the new *Chrysanthemum.*

The photograph at the top of the sheet comprises a side perspective view of a typical flowering stem of 'Zembla Sunny'.

The photograph at the bottom left of the sheet is a close-up view of upper surface of a typical inflorescence and a typical leaf of 'Zembla Sunny'.

The photograph at the bottom right of the sheet is a close-up view of lower surface of a typical inflorescence and a typical leaf of 'Zembla Sunny'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown during the winter and early spring in 's Gravenzande, The Netherlands, under commerical practice in a glass-covered greenhouse. Plants were initially given long day/short night treatments followed by short day/long night treatments to induce flower initiation and development. During production of the plants, day and night temperatures averaged 19° C. and light levels were about 4,000 lux. Plants were grown as spray-types and were about ten weeks from planting when the photographs and the description were taken.

Botanical classification: *Chrysanthemum×morifolium* cultivar Zembla Sunny.

Commercial classification: Decorative-type *Chrysanthemum* typically grown as a spray-type cut flower.

Parentage: Naturally-occurring whole plant mutation of *Chrysanthemum×morifolium* cultivar Zembla, disclosed in U.S. Plant Pat. No. 14,052.

Propagation:

*Type.*—Terminal tip cuttings.

*Time to initiate roots, summer.*—About 5 days at 20° C.

*Time to initiate roots, winter.*—About 6 days at 18° C.

*Time to produce a rooted cutting, summer.*—About 10 days at 20° C.

*Time to produce a rooted cutting, winter.*—About 14 days at 18° C.

*Root description.*—Fine and freely branching; white in color.

Plant description:

*Appearance.*—Herbaceous decorative-type cut *Chrysanthemum*; typically grown as a spray-type; erect and strong flowering stems.

*Growth rate.*—Rapid; vigorous.

*Flowering stem description.*—Length: About 80 cm. Diameter: About 6 mm. Strength: Strong. Aspect: Erect. Color: 146C.

*Foliage description.*—Arrangement: Alternate. Length: About 10 to 13 cm. Width: About 5 to 7.5 cm. Apex: Apiculate. Base: Truncate. Margin: Pinnately lobed; serrate. Texture, upper and lower surface: Pubescent. Petiole length: About 1.5 to 3.5 cm. Color: Developing foliage, upper surface: Closest to 137A. Developing foliage, lower surface: 147B. Fully expanded foliage, upper and lower surfaces: Between 137A and 147A. Venation, upper surface: 147C. Venation, lower surface: 146D. Petiole, upper and lower surfaces: 147C.

Inflorescence description:

*Appearance.*—Decorative-type inflorescence form with oblanceolate to spatulate-shaped ray florets. Inflorescences borne on terminals above foliage. Disk and ray florets develop acropetally on a capitulum. Inflorescences not fragrant. Typically grown as a spray-type.

*Flowering response.*—Under natural conditions, plant typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 51 to 56 days later. Early and uniform flowering response.

*Postproduction longevity.*—Cut inflorescences will maintain good substance and form for about three weeks.

*Quantity of inflorescences per flowering stem.*—About 12 to 18 inflorescences per flowering stem.

*Inflorescence size.*—Diameter: About 7 to 8.5 m. Depth (height): About 3 cm. Diameter of disc: About 5 mm.

*Inflorescence buds.*—Length: About 6 mm. Diameter: About 8 mm. Shape: Globular. Color: 138A.

*Ray florets.*—Length: About 4 cm. Width: About 1.3 cm. Shape: Oblanceolate to spatulate. Apex: Rounded, emarginate. Base: Obtuse; short corolla tube. Margin: Entire. Texture, upper and lower surfaces: Smooth, glabrous; satiny. Number of ray florets per inflorescence: About 200 in multiple whorls. Color: When opening, upper surface: Initially close to 144A; with development, 3A. When opening, lower surface: 5C. Fully opened, upper surface: 5B. Fully opened, lower surface: 5C.

*Disc florets.*—Shape: Tubular. Length: About 6 mm. Width: About 1 mm. Number of disc florets per inflorescence: About 25 to 30. Color, immature and mature: 20A; towards the apex, 145A.

*Peduncles.*—Length, terminal peduncle: About 5.5 cm. Length, fourth peduncle: About 8.5 cm. Diameter: About 2 to 3 mm. Strength: Moderately strong. Texture: Pubescent. Color: 146B.

*Reproductive organs.*—Androecium: Present on disc florets only. Anther color: 12A. Pollen color: 12A. Gynoecium: Present on both ray and disc florets.

*Seed/fruit.*—Seed and fruit production has not been observed.

Disease/pest resistance: Resistance to known *Chrysanthemum* pathogens and pests has not been observed on plants of the new *Chrysanthemum*.

It is claimed:

1. A new and distinct cultivar of *Chrysanthemum* plant named 'Zembla Sunny', as illustrated and described.

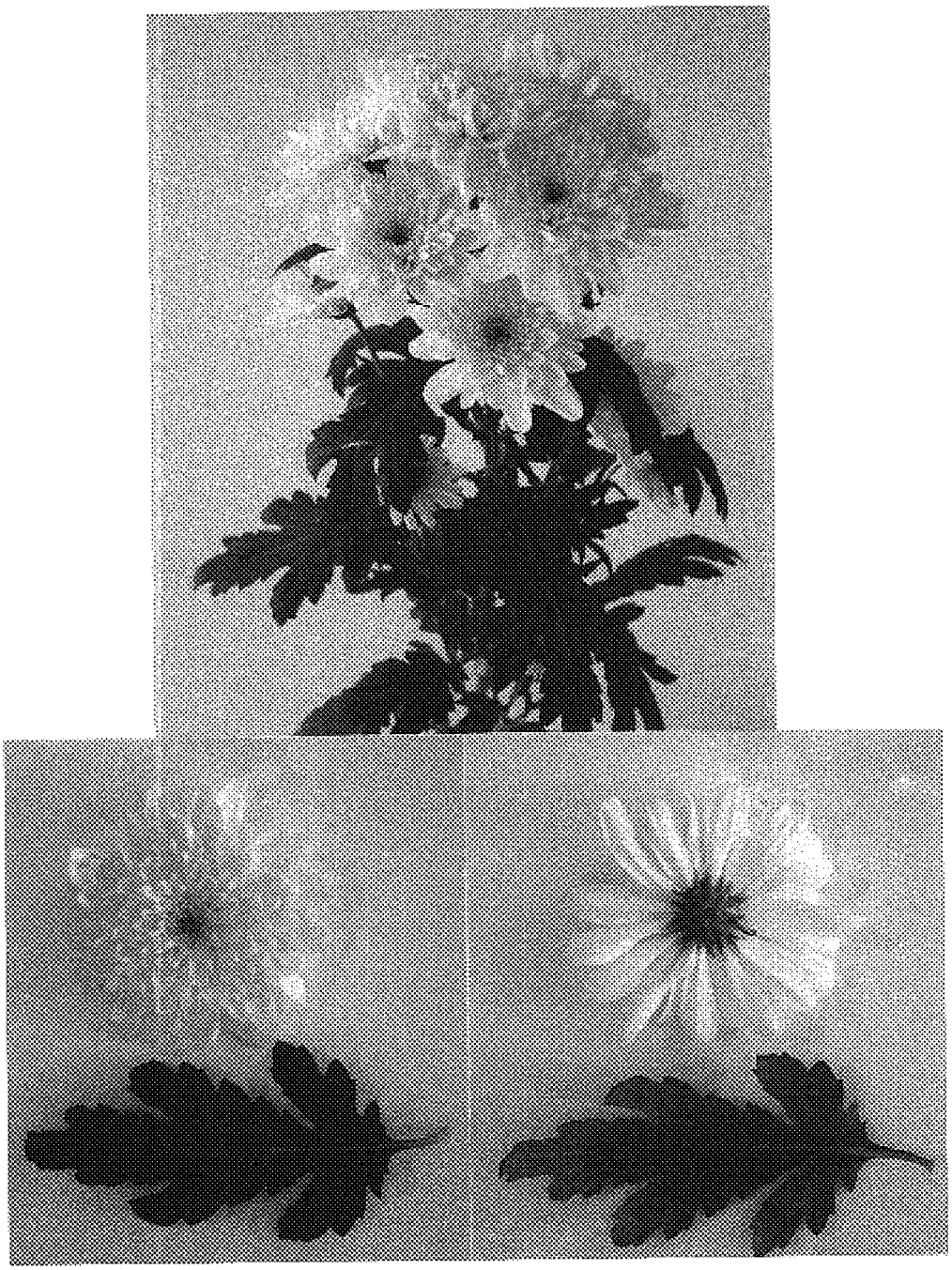

* * * * *